(12) United States Patent
Fujimori et al.

(10) Patent No.: US 7,586,021 B2
(45) Date of Patent: Sep. 8, 2009

(54) NUCLEIC ACID CONSTRUCT, METABOLIC DISORDERED NON-HUMAN ANIMAL AND USE THEREOF

(75) Inventors: Ko Fujimori, Ibaraki (JP); Koichi Saito, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/431,891

(22) Filed: May 11, 2006

(65) Prior Publication Data

US 2006/0277617 A1 Dec. 7, 2006

(30) Foreign Application Priority Data

May 11, 2005 (JP) ............................. 2005-138225

(51) Int. Cl.
*A01K 67/027* (2006.01)
*A01K 67/00* (2006.01)
(52) U.S. Cl. .............................. 800/18; 800/14; 800/8
(58) Field of Classification Search ................... 800/18, 800/14, 8
See application file for complete search history.

(56) References Cited

U.S. PATENT DOCUMENTS

| 6,984,773 | B1 * | 1/2006 | Evans et al. .................... 800/18 |
| 2005/0095677 | A1 * | 5/2005 | Liu et al. .................... 435/69.1 |
| 2006/0247421 | A1 | 11/2006 | Fujimori et al. |

OTHER PUBLICATIONS

Singaraja et al J. Biol. Chem. 276:33969-33979; 2001.*
Houdebine et al. Transgenic Res. 9:305-320; 2000.*
Murray Theriogenology 51: 149-159; 1999.*
Bowie, et al. Science, 247: 1306-10, 1990.*
Skolnick et al. TIBTECH 18:34-39, 2000.*

\* cited by examiner

*Primary Examiner*—Joseph T. Woitach
(74) *Attorney, Agent, or Firm*—Sughrue Mion, PLLC

(57) ABSTRACT

The present invention provides a transgenic non-human animal comprising a human-derived LXRα mutant gene to express a human LXRα mutant protein, wherein the human LXRα mutant is an isoform of LXRα involved in inhibition of normal cholesterol metabolism by normal LXRα; a nucleic acid construct which can be used to produce the transgenic non-human animal; and use thereof.

4 Claims, 2 Drawing Sheets

NUCLEIC ACID CONSTRUCT, METABOLIC DISORDERED NON-HUMAN ANIMAL AND USE THEREOF

BACKGROUND OF THE INVENTION

1. Field of the Invention

The present invention relates to a nucleic acid construct, metabolic disordered non-human animal and use thereof.

2. Description of the Related Art

Cholesterol is an important lipid in an organism, and also a component constituting various lipids. Cholesterol is absorbed via an intestinal tract by ingestion, or bio-synthesized from acetyl-CoA in liver. The bio-synthesized cholesterol is excreted from liver, reabsorbed in small intestine, and transported to liver via blood and re-used. In liver, a part of cholesterol is metabolized into bile acid. When the cholesterol level in vivo rises due to some disorders, hypercholesterolemia occurs, giving causes for onset of hyperlipemia and obesity. The onset mechanism of these diseases originated from hypercholesterolemia has not been elucidated sufficiently.

Reabsorption and conversion into bile acid of cholesterol (cholesterol metabolism) are mediated by respective specific transporters or enzymes. A liver X receptor (LXR) which is one of nuclear receptors is known to be involved in regulation of expression of genes encoding these proteins.

It is so far reported that the liver X receptor (hereinafter, referred to as LXR in some cases) includes two kinds of subtypes (liver X receptor α (hereinafter, referred to as LXRα in some cases), liver X receptor β (hereinafter, referred to as LXRβ in some cases))(see, e.g., Peet et al., Curr. Opin. Genet. Dev. 8; 571-575, 1988). LXRα is known to form a heterodimer with retinoid X receptor (RXR) which is one of nuclear receptors and bind to a transcription regulatory control region of a target gene, to regulate transcription of the target gene.

As a model animal for diabetes and obesity, several animals are provided. For example, ob/ob mouse (leptin knockout mouse) and db/db mouse (leptin receptor knockout mouse) are widely used as a genetically-obese model. These mice cause decrease in energy consumption in addition to increase in energy ingestion by hyperphagia, and express phenotypes such as hyperglycemia, hyperinsulinism, insulin resistance, increase in the weight of a white adipocyte, and the like. These mice are widely used for studies of diabetes and obesity including elucidation of physiological functions and pharmacological functions of leptin. "Obesity" is induced by chronic disproportion of energy ingestion (feeding) and energy consumption, namely, by disorder of energy metabolism, and causes significant increase in lethality as compared with an individual of normal body weight.

On the other hand, for example, Otsuka Long-Evans Tokushima Fatty (OLETF) rat (Kawano K. et al., Diabetes 1992; 41(11): 1422-1428) and ZDF rat (Zucker L. M. et al., Ann. N.Y. Accad. Sci. 1965; 131: 447-458) are widely used as a model for obesity and type II diabetes manifesting insulin resistance. These animals show recognition of decrease in the amount of pancreas β cells in any cases, thus, are used also for studies on fragility of pancreas β cells in onset of type II diabetes.

For covering in detail various symptoms of human obesity and pathologies of diabetes, manufacturing of further new types of diabetes and obesity model animals is required, and needed for investigation of causes and studies of treatment of obesity and diabetes, and the like. A study of application of model animals developed using an embryological engineering strategy is expected as a matter enabling elucidation of pathologies of obesity and diabetes as a multifactorial disease. Further, this is a study field admitted as inevitable since application thereof to development of new therapeutic methods and therapeutic drugs including gene therapy and regenerative medicine in addition to elucidation of onset and pathologies of obesity and diabetes is expected.

SUMMARY OF THE INVENTION

The present invention provides a transgenic non-human animal, specifically a transgenic mouse, comprising a human-derived LXRα mutant (hereinafter, referred to as human LXRα mutant in some cases) gene to express a human LXRα mutant protein, the human LXRα mutant being an isoform of LXRα involved in inhibition of normal cholesterol metabolism by normal type LXRα. In this transgenic animal, remarkably high body weight increase and blood cholesterol increase are recognized and remarkable accumulation of visceral fat is observed after ingestion of high-fat diet in comparison with a wild-type animal. Thus, this transgenic animal can be a new type of model animal for diabetes and obesity. This transgenic animal is useful in the field of development of medicinal products and foods and the like for diseases accompanied by obesity.

That is, the present invention provides:

1. a nucleic acid construct comprising a polynucleotide encoding an isoform of human-derived liver X receptor α, wherein at least one element selected from the element group consisting of promoters, response elements and enhancer elements is operably linked to said polynucleotide, and wherein said isoform of human-derived liver X receptor α is a liver X receptor α mutant protein (hereinafter, referred to as the present LXRα mutant protein in some cases) comprising at least an amino acid sequence encoded by exon 5 of a liver X receptor α gene (hereinafter, referred to as nucleic acid construct of the present invention in some cases);

2. the nucleic acid construct according to the above 1, wherein the isoform of human-derived liver X receptor α is a liver X receptor α mutant protein comprising any of the following amino acid sequences:

(1) the amino acid sequence of SEQ ID NO: 1

(2) an amino acid sequence substantially identical to the amino acid sequence of SEQ ID NO: 1, and (3) an amino acid sequence having an amino acid identity of 95% or more to the amino acid sequence of SEQ ID NO: 1;

3. the nucleic acid construct according to the above 1 or 2, wherein the selected element is a liver-specific promoter;

4. the nucleic acid construct according to the above 1 or 2, wherein the selected elements are a liver-specific promoter and an enhancer element for said promoter;

5. the nucleic acid construct according to the above 1 or 2, wherein the selected elements are a promoter of a mouse-derived albumin gene and an enhancer element for said promoter:

6. a method for producing a non-human animal or part thereof expressing an isoform of human-derived liver X receptor α, comprising a step of introducing the nucleic acid construct according to any of the above 1 to 5 into a non-human animal or part thereof (hereinafter, referred to as production method of the present invention in some cases);

7. a method for producing a non-human animal or part thereof expressing an isoform of human-derived liver X receptor α, comprising a step of introducing the nucleic acid construct according to any of the above 1 to 5 into a genome of a non-human animal;

8. a non-human animal or its progeny or part thereof, which comprises the nucleic acid construct according to any of the above 1 to 5 (hereinafter, referred to as non-human animal or the like of the present invention in some cases);

9. a non-human animal or its progeny, which comprises the nucleic acid construct according to any of the above 1 to 5 (hereinafter, referred to as non-human animal of the present invention in some cases);

10. a non-human animal or its progeny or part thereof, produced by the production method according to the above 6 or 7;

11. a non-human animal or its progeny, produced by the production method according to the above 6 or 7;

12. a non-human animal or its progeny or part thereof, produced by crossing a first non-human animal or its progeny according to the above 9 or 11 with a second non-human animal which is the same species as the first non-human animal and is another type of diabetes or obesity model;

13. a non-human animal or its progeny, produced by crossing a first non-human animal or its progeny according to the above 9 or 11 with a second non-human animal which is the same species as the first non-human animal and is another type of diabetes or obesity model;

14. an assay method for the anti-obesity ability of a substance (hereinafter, referred to as assay method of the present invention in some cases), comprising (1) a first step of bringing a test substance into contact with a non-human animal or its progeny according to the above 9, 11 or 13 or a non-human animal or its progeny or part thereof according to the above 8, 10 or 12, (2) a second step of measuring the expression amount of a human LXRα mutant protein in the non-human animal or its progeny or part thereof contacted with the test substance or an index value having a correlation with the expression amount, and comparing the measured amount or value with a control, and (3) a third step of evaluating the anti-obesity ability of the test substance based on the comparison result in the second step;

15. an assay method for the anti-obesity ability of a substance, comprising administering a test substance to a non-human animal or its progeny according to the above 9, 11 or 13, measuring the presence or absence of variation or the extent of the variation in blood cholesterol level of the non-human animal or the progeny, and evaluating the anti-obesity ability of said test substance based on the measured result (hereinafter, referred to as first assay method of the present invention in some cases);

16. an assay method for the anti-obesity ability of a substance, comprising bringing a test substance into contact with a non-human animal or its progeny or part thereof according to the above 8, 10 or 12, measuring the presence or absence of variation in the expression amount of a liver X receptor α mutant protein having at least an amino acid sequence encoded by exon 5 of a liver X receptor α gene in the non-human animal or the progeny or part thereof contacted with said test substance or an index value having a correlation with the expression amount or the extent of the variation, and evaluating the anti-obesity ability of said test substance based on the measured result (hereinafter, referred to as second assay method of the present invention in some cases);

17. a method for searching a substance having an anti-obesity ability, comprising selecting a test substance having an anti-obesity ability based on the anti-obesity ability evaluated by the assay method according to the above 14, 15 or 16 (hereinafter, referred to as searching method of the present invention in some cases);

18. an anti-obesity agent, comprising as an active ingredient the substance having an anti-obesity ability selected by the searching method according to the above 17 (hereinafter, referred to as anti-obesity agent of the present invention in some cases), and the like.

DETAILED DESCRIPTION OF THE PREFERRED EMBODIMENTS

Figure 1:
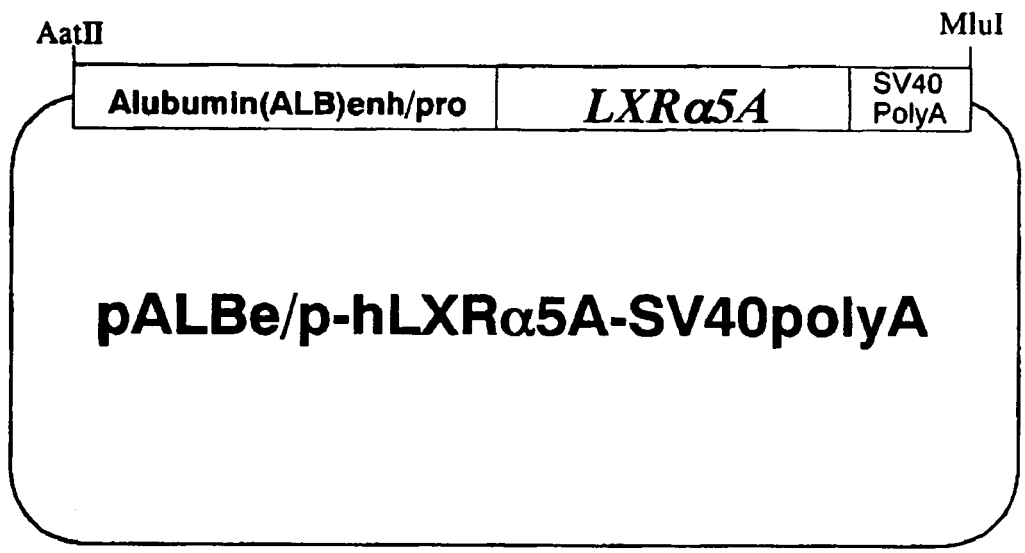
FIG. 1 is a view showing a restriction enzyme map of pALBe/p-hLXRα5A-SV40PolyA.

The present invention will be explained in detail below.

The present LXRα mutant proteins are isoforms of a LXRα described in, for example, EP1630174A1, and contain at least an amino acid sequence encoded by exon 5.

Representative examples include an isoform of a LXRα in which an amino acid sequence encoded by intron 5 of a LXRα gene is contained (i.e. the present LXRα mutant 5A protein), an isoform of a LXRα in which an amino acid sequence encoded by a portion of intron 6 of a LXRα gene is contained (i.e. the present LXRα mutant 6A protein) and the like.

Further, specifically, examples of the present LXRa mutant 5A protein include a LXRα isoform comprising any amino acid sequence of (1) the amino acid sequence represented by SEQ ID NO: 1, (2) an amino acid sequence which is substantially identical to the amino acid sequence of SEQ ID NO: 1, and (3) an amino acid sequence which has 95% or more amino acid identity with the amino acid sequence of SEQ ID NO: 1. In addition, examples of the present LXRα mutant 6A protein include a LXRα isoform comprising any amino acid sequence of (1) the amino acid sequence of SEQ ID NO: 2, (2) an amino acid sequence which is substantially identical to the amino acid sequence of SEQ ID NO: 2, and (3) an amino acid sequence which has 95% or more amino acid identity with the amino acid sequence of SEQ ID NO: 2.

Such the present LXRα mutant protein has weaker transcription activating ability as compared with ligand-dependent transcription activating ability of a normal LXRα.

The present LXRα mutant 5A protein has an amino acid sequence identical to that of normal type except that an amino acid sequence encoded by intron 5 is contained downstream of an amino acid residue corresponding to the carboxyl terminus of an amino acid sequence encoded by exon 5 of a normal LXRα. The transcription activating ability of these LXRα mutant proteins depending on 22R-oxycholesterol that is one of ligands for a LXRα, is at an extremely weak or not recognized level as compared with the transcription activating ability possessed by a normal LXRα. Further, when a normal LXRα and the aforementioned each LXRα mutant proteins are coexpressed, ligand-dependent transcription activation observed when only a normal LXRα is expressed, is remarkably suppressed. From the above findings, it is understandable that the present LXRα mutant proteins are involved in inhibition of normal cholesterol metabolism by a normal LXRα in a dominant negative manner in vivo.

Herein, regarding definition of "an amino acid sequence which is substantially identical to", it is the well-known fact that, generally, in the case where an amino acid sequence of a protein having physiological activity is slightly changed, for example, even in the case where there is a change such as deletion, substitution and addition of one or a plurality of amino acids in the amino acid sequence, physiological activity of the protein is maintained in some cases. Therefore, "an amino acid sequence which is substantially identical to" referred in the present specification means that, as far as biological activity substantially equivalent to that of a particular amino acid sequence (i.e. amino acid sequence of SEQ ID NO: 1 or 2) is retained, a human LXRα mutant protein in which one or a plurality of amino acids in the amino acids sequence have been deleted, substituted or added is also included in the scope of the present invention. The number of amino acids to be altered in the foregoing is at least one residue, specifically, one or several (herein, "several" is around 2 to about 10) or more. Such the number of alterations may be in such the range that physiological activity of the protein is maintained. More specifically, it is a human LXRα mutant protein in which one or more and 20 or less, preferably one or more and 10 or less, further preferably one or more and 5 or less amino acids in the amino acid sequence of SEQ ID NO: 1 or 2 are deleted, substituted or added. Such the mutation may be, for example, a naturally occurring mutation resulting from processing which a protein undergoes in a cell, a difference in species of an organism, individuals, organs, tissues, or the like from which the protein is derived, or may be an artificial amino acid mutation (e.g. mutation in an amino acid present in an amino acid sequence of a protein produced by introducing a mutation into DNA encoding a natural protein by site-directed mutagenesis, mutagenic treatment or the like, followed by expressing it).

Such the mutant protein generated by deletion, substitution or addition of amino acids may contain a conservatively substituted amino acid sequence. This means that a particular amino acid residue may be substituted with a residue having physiochemical similarility (e.g. nature similar in hydrophobicity, charge, pK, stereo-structural feature and the like). Non-limiting examples of such the conservative substitution include substitution between aliphatic chain-containing amino acid residues, and substitution between polar groups, such as substitution in groups of (1) glycine, alanine; (2) valine, isoleucine, leucine; (3) aspartic acid, glutamic acid, asparagine, glutamine; (4) serine, threonine; (5) lysine, arginine; (6) phenylalanine, tyrosine.

A mutant protein generated by deletion, substitution or addition of an amino acid can be obtained by performing, for example, site-directed mutagenesis which is the known technique (e.g. Nelson and McClelland, Methods Enzymol, 216; 279, 1992, a method of utilizing amber mutation (gapped-duplex method, Nucleic Acids Res., 12, 9441-9456, 1984), a method by PCR using a primer for introducing mutation) on a gene comprising a nucleotide sequence encoding an amino acid sequence thereof.

Site-directed mutagenesis can be performed by using a synthetic primer containing mutation to be introduced. That is, using the aforementioned synthetic oligonucleotide and a primer having a nucleotide sequence complementary to a nucleotide sequence thereof as primers, and employing a plasmid comprising a gene of a normal LXRα as a template, an amplification reaction is performed. Then, treatment with DpnI which is a methylation-sensitive restriction enzyme leaves only a newly generated DNA having the mutation. Using this reaction solution, *Escherichia coli* XLI-Blue strain is transformed, and spread on an ampicillin-containing LB agar medium. This is cultured at 37° C. overnight, and a plasmid is isolated from the grown colony. Thereby, a plasmid comprising a mutated DNA can be obtained. As a kit based on the aforementioned method, for example, QuickChange Site-Directed Mutagenesis Kit (manufactured by Stratagene Corporation) or the like is commercially available, and this may be utilized. Introduction of intended mutation can be confirmed by determining a nucleotide sequence thereof.

Further, examples of a method of performing deletion, substitution or addition of an amino acid sequence include a method of treating a gene with a mutagen, and a method of cleaving a gene with a restriction enzyme, followed by removing, adding or substituting a selected gene fragment, and further followed by ligating it, in addition to the aforementioned site-directed mutagenesis.

Herein, "normal LXRα" means a LXRα comprising an amino acid sequence which occurrs in nature most frequently in amino acid sequences of the receptor protein derived from an organism of the same species. Examples of a human-derived normal LXRα include a LXRα comprising an amino acid sequence registered in public database (GenBank Accession No. NM_005693).

"Amino acid identity", and "nucleotide identity" in the present invention refer to identity and homology of sequences between two proteins or two DNAs. The "identity" is determined by comparing two sequences aligned in the optimal state, over an entire region of sequences to be compared. Herein, proteins or DNAs to be compared may have addition or deletion (e.g. gap etc.) in the optimal alignment of two sequences. Such the identity can be calculated, for example, by producing an alignment using Vector NTI utilizing Clustal W algorithm (Nucleic Acid Res., 22(22): 4673-4680 (1994). The identity is measured using a sequence analyzing software, specifically, Vector NTI, GENETYX-MAC, or an analyzing tool provided by public databases. The public databases are generally available, for example, at the Web site of the DNA Data Bank of Japan (the international databank operated within the Center for Information Biology and DNA Data Bank of Japan).

"Amino acid identity" in the present invention is based on an amino acid sequence, and is preferably, for example, about 95% or more. "Nucleotide identity" is based on a nucleotide sequence, and is preferably, for example, about 95% or more.

The polynucleotide comprising a nucleotide sequence encoding an amino acid sequence of the present LXRα mutant protein (i.e. the present LXRα mutant gene) can be obtained by the conventional genetic engineering method such as a hybridization method and a PCR method.

For example, RNA is extracted from an animal tissue of a mammal such as human, monkey, rabbit, rat, mouse and the like or a cultured cell derived from such the animal according to the genetic engineering method described in such as Sambrook and Russell; Molecular Cloning $3^{rd}$ edition, Cold Spring Harbor Laboratory (2001), and a single-stranded cDNA is synthesized. Specifically, for example, a tissue such as liver is homogenized in a solution containing a protein denaturing agent such as guanidine thiocyanate and, further, chloroform or the like is added to the homogenate to denature proteins. After the denatured proteins are removed by centrifugation, total RNA is extracted from the recovered supernatant fraction using phenol, chloroform or the like. Examples of a commercially available kit based on these methods include ISOGEN (manufactured by Nippon Gene Co., Ltd.), and TRIZOL reagent (manufactured by Invitrogen Corporation).

The resulting total RNA is used as a template to anneal an oligo dT primer to a poly A sequence of mRNA, and a reverse transcriptase such as RNaseH-Superscript II Reverse Transcriptase (manufactured by Invitrogen Corporation), and attached buffer and oligo dT primer are used to perform a reaction at 42° C. for 1 hour and, then, this is heated at 99° C. for 5 minutes to inactivate the reverse transcriptase. Then, mRNA-strand is nicked with RNaseH and, using the single-stranded cDNA as a template, double-stranded cDNA is synthesized with *Escherichia coli* DNA polymerase I. Ends of the resulting double-stranded cDNA are made blunt with T4 DNA polymerase. The blunt-ended double-stranded cDNA is inserted into pBluescript II vector or bacteriophage, for example, a vector such as λgt11, EMBL3 and the like, by T4 ligase to prepare a cDNA library. Examples of a commercially available kit based on these methods include cDNA Synthesis System Plus (manufactured by Amersham Biosciences Corporation) and TimeSaver cDNA Synthesis Kit (manufactured by Amersham Biosciences Corporation). From the thus prepared cDNA library, hybridization is performed, for example, using a DNA having a partial nucleotide sequence of the nucleotide sequence of human-derived LXRα mutant 5A gene (SEQ ID NO: 3, 4, 5 or 6) as a probe. Examples of the hybridization condition include the condition under which hybridization is performed under the stringent condition. Hybridization can be performed according to a conventional method described, for example, in Sambrook and Russell; Molecular Cloning $3^{rd}$ edition, Cold Spring Harbor Laboratory (2001). Examples of the "under the stringent condition" include the condition under which a hybrid is formed at 45° C. in a solution containing 6×SSC (a solution containing 1.5 M NaCl and 0.15 M trisodium citrate is 10×SSC), and then washed at 50° C. with 2×SSC (Molecular Biology, John Wiley & Sons, N.Y. (1989), 6.3.1-6.3.6), and the condition under which a hybrid is formed in a solution containing 50% formamide, 6×SSC, 5×Denhart solution, 0.5% (w/v) SDS and a heat-denatured salmon sperm DNA (100 μg/ml) by incubating at 42° C. overnight using the aforementioned probe (10×$10^6$ cpm/ml) labeled with [α-$^{32}$P] dCTP by a random priming method, and then washed in 2×SSC containing 0.1% (w/v) SDS at room temperature for 10 minutes and, further, washed in 0.2×SSC containing 0.1% (w/v) SDS at 55° C. for 10 minutes twice. In addition, a salt concentration in the washing step may be selected, for example, from the condition of around 2×SSC at about 50° C. (low stringency condition) to the condition of around 0.2× SSC and about 50° C. (high stringency condition). A temperature at a washing step can be selected, for example, from room temperature (low stringency condition) to 65° C. (high stringency condition). Alternatively, both of the salt concentration and temperature may be varied.

Then, a signal is detected with a X-ray film (e.g. Hyperfilm-MP; manufactured by Amersham Biosciences Corporation) or a bioimaging system (BAS-2000; manufactured by Fuji Photo Film Co., Ltd.), and a recombinant comprising a vector comprising a nucleotide sequence which binds with a probe can be obtained.

When a primer for a PCR method is designed, two may be selected from, for example, the nucleotide sequence of human-derived LXRα mutant 5A gene (SEQ ID NO: 3, 4, 5 or 6), for example, so that the following conditions are satisfied.

1) A length of a primer is 15 bases to 40 bases, preferably 20 bases to 30 bases.

2) A ratio of guanine and cytosine in a primer is 40% to 60%, preferably 45% to 55%, more preferably 50% to 55%.

3) In a primer sequence, a distribution of adenine, thymine, guanine and cytosine is not partially biased. For example, a region where guanine and cytosine are repeated is not suitable.

4) A distance on a nucleotide sequence of a gene corresponding to a selected primer is preferably 100 bases to 3000 bases, further preferably 100 bases to 500 bases.

5) There is no complementary sequence in each primer itself, or between two primers.

Once a nucleotide sequence of a primer is selected, a primer may be chemically synthesized by a commercially available DNA synthesizer.

For example, there is a combination using a primer comprising the nucleotide sequence of SEQ ID NO: 7 as a sense primer, and a primer comprising the nucleotide sequence of SEQ ID NO: 8 as an antisense primer. As the condition for PCR, for example, primers are added to a reaction solution so that each of them becomes 200 nM, and PCR is performed by employing the above-synthesized single-stranded cDNA as a template and, for example, using LA Taq DNA polymerase (manufactured by TAKARA SHUZO Co., Ltd.) and a reaction buffer attached to the enzyme. As such the PCR, for example, heat denaturation is performed at 95° C. for 3 minutes and, thereafter, around 35 cycles is performed, one cycle being 94° C. for 30 seconds, 55° C. for 30 seconds, and 72° C. for 1 minute. Herein, in place of the cDNA synthesized as described above, a commercially available cDNA derived from various animals such as QUICK-Clone cDNA manufactured by Clontech Laboratories, Inc. may be used. An aliquot of the resulting reaction solution is analyzed by agarose gel electrophoresis, and an intended band is cloned into pGEM-T Easy vector (manufactured by Promega Corporation) by a TA cloning system, directly or after excision from the gel. A nucleotide sequence of the inserted DNA fragment can be determined and confirmed by the Dye Terminator method.

The polynucleotide comprising a nucleotide sequence encoding an amino acid sequence of the present LXRα mutant protein (i.e. the present LXRα mutant gene) can be thus obtained. The present LXRα mutant gene may be introduced into a vector which can be utilized in a host cell to be transformed. For example, a vector comprising the present LXRα mutant gene can be constructed by incorporating according to the conventional genetic engineering procedure into a vector which can be autonomously replicated in a host cell, which can be isolated and purified from a host cell, and which has a detectable marker. Examples of a vector comprising the present LXRα mutant gene may include plasmids such as pUC19 (manufactured by TAKARA SHUZO Co., Ltd.) and pBluescript II (Stratagene Corporation), specifically when *Escherichia coli* is a host cell. When budding yeast is a host cell, plasmids such as pACT2 (manufactured by Clontech Laboratories, Inc.) and pYES2 (manufactured by Invitrogen Corporation) may be exemplified. In addition, when a mammal cell is a host cell, plasmids such as pRc/RSV and pRc/CMV (Invitrogen Corporation) may be exemplified.

The present LXRα mutant protein may be prepared as a natural protein by a procedure such as extraction and purification from a naturally occurring organism, or may be prepared as a recombinant protein by using a genetic engineering procedure. For example, a purified protein can be prepared by preparing a crude extract from a human cell or tissue, and using various columns. Herein, a cell is not particularly limited as far as it produces and expresses the present LXRα mutant protein, but for example, a liver-derived cell, a kidney-derived cell and the like can be used. In addition, among the splicing mutant proteins of the present invention, a protein which is produced and expressed in an organism other than a human can be prepared from the organism.

In order to prepare the present LXRα mutant protein, the present LXRα mutant gene or the like is transformed into a suitable host cell as described above, and the transformant (i.e. the present transformant) is cultured, thereby, a LXRα mutant protein may be produced. The produced LXRα mutant protein is recovered according to a conventional method. The recovered present LXRα mutant protein is purified by a suitable method depending on the purpose. For example, when the present transformant is a microorganism, the transformant is cultured using various media appropriately containing a carbon source, a nitrogen source, organic salts, inorganic salts and the like, which are used in conventional culture in general microorganisms. Culturing is performed according to a conventional method in general microorganisms, and solid culture, liquid culture (test tube shaking culture, reciprocating shaking culture, Jar Fermenter culture, tank culture etc.) and the like are possible. A culture temperature can be appropriately changed in such a range that a microorganism is grown. For example, culture is generally performed at a culture temperature of about 15° C. to about 40° C., in a culture medium at a pH of about 6 to about 8. A culture time is different depending on culture condition, and is usually about 1 hour to about 24 hours. When an inducible promoter is used, an induction time is desirably within one day, usually a few hours.

In addition, when the transformant is an animal cell such as a mammal, an insect and the like, the transformant can be cultured using a culture medium used in conventional culture in general cultured cells. In the case of an animal cell, for example, the cell may be cultured under the condition of 37° C. and the presence of 5% $CO_2$ using a liquid medium (manufactured by such as Invitrogen Corporation) to which Fetal Bovine Serum (FBS) has been added to a final concentration of about 5% (v/v) to about 10% (v/v). When cells are grown to confluent, for example, an around 0.25% (v/v) trypsin/PBS solution is added to disperse into individual cells, this is diluted a few-fold and seeded on a new dish, and further cultured. In the case of an insect cell, similarly, for example, the cell maybe cultured at a culture temperature of about 25° C. to about 30° C. using the Grace medium containing 10% (v/v) FBS or a serum-free medium such as SF-900 (manufactured by Invitrogen Corporation) and the like. In addition, when a recombinant virus vector such as Baculovirus is used, it is desirable to recover a cell within 72 hours after infection.

Recovering of the present LXRα mutant protein produced by the present transformant may be performed by appropriate combination of conventional isolation and purification methods. For example, a fraction containing the intended present LXRα mutant protein can be obtained by, after completion of culture, collecting cells of the transformant by centrifugation or the like, suspending the collected cells in a conventional buffer, for example, PBS containing an appropriate protease inhibitor, homogenizing the cells by ultrasonic treatment, a Dounce homogenizer or the like, centrifuging the homogenate at 20,000×g for a few tens of minutes to about 1 hour, and recovering the supernatant fraction. Further, the more purified intended present LXRα mutant protein may be recovered from the supernatant fraction by subjecting to various chromatographies by the conventional protein purifying technique.

The nucleic acid construct of the present invention is characterized in that it comprises a polynucleotide encoding an isoform of human-derived liver X receptor α, wherein at least one element selected from the element group consisting of promoters, response elements and enhancer elements is operably linked to said polynucleotide, and wherein said isoform of human-derived liver X receptor α is a liver X receptor α mutant protein comprising at least an amino acid sequence encoded by exon 5 of a liver X receptor α gene (that is, the present LXRα mutant protein).

Here, when referring to "isoform of human-derived liver X receptor α", the isoform of human-derived liver X receptor α is a liver X receptor α mutant protein comprising at least an amino acid sequence encoded by exon 5 of a liver X receptor α gene (that is, the present LXRα mutant protein), and specific examples of the isoform of human-derived liver X receptor α includes liver X receptor α mutant proteins having any of the following amino acid sequences:

(1) amino acid sequence of SEQ ID NO: 1

(2) amino acid sequence substantially identical to amino acid sequence of SEQ ID NO: 1, and (3) amino acid sequence having an amino acid identity of 95% or more to amino acid sequence of SEQ ID NO: 1.

Such the present LXRα mutant protein has weaker transcription activating ability as compared with ligand-dependent transcription activating ability of a normal LXRα.

"Element" includes one or more elements selected from the element group consisting of promoters, response elements and enhancer elements, and examples thereof include a liver-specific promoter, a liver specific promoter and enhancer element for said promoter (specifically, a promoter of a mouse-derived albumin gene and enhancer for said promoter), and the like.

For producing the nucleic acid construct of the present invention, first, at least one element selected from the element group consisting of promoters, response elements and enhancer elements capable of functioning in a host cell is operably linked to an upstream of a polynucleotide comprising a nucleotide sequence encoding an amino acid sequence of the present LXRα mutant protein prepared as described above (namely, the present LXRα mutant gene). The construct thus obtained may be incorporated into, for example, a vector such as a transfer vector and the like for producing a transgenic mouse, thereby, constructing a vector capable of expressing the present LXRα mutant gene in a host cell. Further, it is also possible to link a polyA additional sequence and the like necessary for termination of transcription to a downstream of a polynucleotide having a nucleotide sequence coding an amino acid sequence of the present LXRα mutant protein (namely, the present LXRα mutant gene).

Here, "operably linked" means that the aforementioned element and the present LXRα mutant gene are linked so that the present LXRα mutant gene is expressed under control of the element in a host cell into which the present LXRα mutant gene is transferred. The element to be used shows an element activity in a host cell to be transformed and examples thereof include a liver-specific promoter, a liver-specific promoter and enhancer element for said promoter (specifically, a promoter of a mouse-derived albumin gene and enhancer for said promoter), Rous sarcoma virus (RSV) promoter, Cytomegalovirus (CMV) promoter, Simianvirus (SV) 40 promoter and the like. "Transfer vector" means a vector used for inserting an intended DNA into a random position on a genome of a host cell, and as the transfer vector, commercially available expression vectors can also be used.

When a vector harboring in advance an element operable in a host cell is used, the present LXRα mutant gene may be inserted into a downstream of the element so that the element harbored by the vector and the present LXRα mutant gene are operably linked. For example, in the aforementioned plasmids pRc/RSV, pRc/CMV and the like, a cloning site is provided downstream of a promoter operable in an animal cell, and when the present LXRα mutant gene is inserted into the cloning site and introduced into an animal cell, the present LXRα mutant gene can be expressed.

By introducing the present LXRα mutant gene or the like into a host cell, the present transformant can be obtained. As a method of introducing the present LXRα mutant gene or the like into a host cell, a conventional introducing method can be applied depending on a host cell to be transformed. For example, when *Escherichia coli* which is a microorganism is a host cell, a conventional method can be used, such as a calcium chloride method, an electroporation method and the like described in Molecular Cloning $3^{rd}$ edition (Sambrook and Russell, Cold Spring Harbor Laboratory, 2001. In addition, when a mammal cell or an insect cell is a host cell, the gene or the like can be introduced into the cell by a conventional gene transfection method such as a calcium phosphate method, an electroporation method and a lipofection method. Alternatively, the present LXRα mutant gene may be expressed using yeast as a host cell. In this case, preferably, budding yeast (e.g. *Saccharomyces cereviciae*) is used, and yeast such as *Pichia* and the like may be also used. Examples of a method of transforming yeast include the method of Ito et al. (J. Bacteriol. 153; 163-168, 1983).

In order to incorporate the present LXRα mutant gene into a virus such as Baculovirus and Vacciniavirus, a transfer vector can be used, which contains a nucleotide sequence homologous with a genome of a virus to be used. Examples of such the transfer vector include plasmids such as pVL1392, pVL1393 (manufactured by Invitrogen Corporation) and the like. When the present LXRα mutant gene is inserted into the aforementioned transfer vector, and the transfer vector and a virus genome are introduced simultaneously into a host cell, homologous recombination occurs between the transfer vector and the virus genome, and a recombinant virus in which the present LXRα mutant gene is incorporated into the genome can be obtained. As the virus genome, genomes of Baculovirus, Adenovirus and the like can be used. When a virus is used as a vector, as described above, a virus DNA can be introduced into a host cell by a conventional gene transfection method, or alternatively, a virus DNA can be also introduced into a host cell by directly infecting a host cell with a recombinant virus.

As the non-human animal in the present invention, for example, non-human mammal animals (e.g., rabbit, dog, cat, guinea pig, hamster, mouse, rat, sheep, goat, pig, horse, cow, monkey etc.) and the like are used, of them, Rodent mammal animals such as mouse, rat, guinea pig and the like are preferable, and mouse and rat are particularly suitable.

A part of a non-human animal in the present invention is not particularly restricted providing it is a cell or tissue derived from the animal, and examples thereof include parts of a body such as fat tissues such as epididymal fat tissue, retroperitoneal adipose tissue, mesenterium adipose tissue, subcutaneous adipose tissue, brown adipose tissue and the like, further, other tissues of heart, lung, kidney, cholecystis, liver, pancreas, spleen, bowel, testis (orchis), ovary, uterus, placenta, muscle, blood vessel, brain, pulpa, thyroid gland, thymus, mammary gland and the like. Body fluid such as blood, lymph, urine and the like originated from the animals are also included in the part of a non-human animal in the present invention.

Further, culture cells obtained by isolating and culturing cells contained in the above-mentioned tissues, organs and body fluid (including collected primary cells and cells established from the primary cells) and extracts thereof, additionally, organs at developmental stage in embryo, and cultures of associated cells, and ES cells, are also included in the part of a non-human animal irrespective of the presence or absence of a differentiation and proliferation ability.

A non-human animal or its progeny (namely, non-human animal of the present invention) or part thereof characterized by comprising a nucleic acid construct of the present invention (namely, these are collectively referred to as non-human animal and the like of the present invention) may be advantageously produced by introducing a nucleic acid construct of the present invention into a non-human animal or part thereof. Preferably, it is advantages to introduce a nucleic acid construct of the present invention into a genome of a non-human animal. Here, as the aforementioned progeny, for example, non-human animals of n-th generation (n is 1 or more) experienced sib mating, and the like are mentioned.

Introduction of a nucleic acid construct of the present invention into a non-human animal or part thereof may be advantageously carried out by conventional methods such as known transgenic animal production methods and gene transfection methods (see, e.g., Production of Transgenic Mouse: for example, Matsumura Masami, Yamamoto Masaru, "Experimental Medicine supplementary volume, newly corrected, Genetic Engineering Hand Book, revision vol. 3" (1999, published by Yodo sha), 234-238), Tsujimoto Gozo, Tanaka Toshio, "Experimental Medicine supplementary volume, Genome Function Study Protocol" (2000, published by Yodo sha), 222-227, etc.) and the like. Specifically, for example, it is effective that DNA coding a human LXRα mutant protein is introduced into a random position on a genome of a non-human animal cell, to produce an intended transgenic mouse. This method can be applied to mouse, rat, rabbit, pig and the like.

A fertilized ovum comprising thus introduced nucleic acid construct of the present invention is placed in an uterus of a pseudopregnent allomother and childbirth is caused, then, DNA is extracted from a part of a body of the resultant borne child (for example, caudal edge, etc.) and the like. Carrying out Southern blot analysis, PCR analysis and the like using the extracted DNA as a sample confirms that intended exogenous DNA contained in the nucleic acid construct of the present invention is transmitted to a progeny (preferably, integrated into a genome of a host cell).

Furthermore, a novel non-human animal or its progeny or part thereof may be produced by, for example, crossing a first non-human animal or its progeny thus produced with a second non-human animal which is the same species as the first non-human animal and is another type of diabetes or obesity model.

Also regarding thus produced progeny (F1), DNA is extracted from a part of a body (for example, caudal edge). Southern blot analysis, PCR analysis and the like using the extracted DNA as a sample confirms that intended foreign DNA contained in the nucleic acid construct of the present invention is transmitted to a progeny. Furthermore, increase and decrease in the expression amount of a gene encoding a LXRα mutant protein can be checked by carrying out real-time PCR quantitative analysis or northern blot analysis using as a sample an RNA extract from an embryo or a part of a body such as various fat tissues such as epididymal fat tissue, retroperitoneal adipose tissue, mesenterium adipose tissue, subcutaneous adipose tissue, brown adipose tissue and the like, further, other tissues of heart, lung, kidney, cholecystis, liver, pancreas, spleen, bowel, testis (orchis), ovary, uterus, placenta, muscle, blood vessel, brain, pulpa, thyroid gland, thymus, mammary gland and the like, and comparing the results. Besides, increase and decrease in the amount of a LXRα mutant 5A protein can be checked by carrying out an ELISA (Enzyme-linked Immunosorbent Assay) method using as a sample a part of the aforementioned tissues (homogenate, section and the like) or body fluid (blood, urine and the like), and comparing the results.

In thus produced non-human animal or its progeny (namely, non-human animal of the present invention), breeding under load of ingestion of a normal diet or high-fat diet is carried out, then, OGTT (oral glucose tolerance test: variation of blood glucose level and insulin level is observed after a certain amount of sugar is loaded) and ITT (insulin tolerance test: variation of blood glucose level and insulin level is observed after a certain amount of insulin is loaded), various blood/urine tests (analysis of parameters of sugar metabolism and fat metabolism), various histopathological analyses (change in the weight of various fat tissues, liver, kidney, spleen, muscle, blood vessel and the like, alternatively, sections of these tissues are dyed, and conditions of fat cells, liver cells or pancreas Langerhans β cells, in addition , insulin amount, glycogen amount and the like, are observed), and the like are carried out, and a difference in physiological activity between a non-human animal of the present invention and a wild-type non-human animal is checked.

As a result, as shown in examples described later, a non-human animal of the present invention (for example, 8-week old) shows findings such as increase in body weight, increase in blood cholesterol level and remarkable accumulation of visceral fat by after ingestion of a high-fat diet (for example, 16-week old). From these findings, it is understandable that the non-human animal of the present invention causes accumulation of visceral fat with disorder of cholesterol metabolism, and expresses a phenotype of obesity.

Therefore, the non-human animal of the present invention is used as a model animal for a disease associated with obesity, and for example, when a non-human animal of the present invention or part thereof and a wild-type non-human animal or part thereof are compared (for example, using methods such as real-time PCR quantitative analysis, northern blot analysis and the like), it becomes possible to know difference in onset conditions of a disease associated with obesity, to identify a gene of which expression is induced or suppressed in this tissue, further, to search a marker gene of which expression varies in a disease associated with obesity from the result, eventually, to give an index for elucidation of causes of a disease, and the like. Furthermore, by carrying out observation of growth differentiation, development and life action, histopathological test or biochemical test in a period from embryonic period to mortality of a non-human animal of the present invention or part thereof, further detailed pathological analysis can be conducted also on a disease correlated with a LXRα mutant protein (referring, for example, to "Transgenic Animal", Yamamura Kenichi et al., (Kyoritsu Shuppan K.K.)). Still further, it can also be used for evaluating an obesity improvement effect or onset prevention effect of a medicinal product, food, medicinal product candidate substance, food candidate substance and the like. As "obesity improvement effects", for example, effect of improving body weight increase, blood cholesterol increase, accumulation of visceral fat, and the like, which are characteristic conditions of obesity, are mentioned. "Obesity improvement effect or onset prevention effect" represents an ability of controlling glycolysis, gluconeogenesis and glucose incorporation (saccharometabolism-controlling ability) in a liver or fat tissue, or an ability of controlling fat synthesis or lipolysis (fatty acid synthesis and/or fatty acid metabolism-controlling ability). Additionally, an ability of controlling cholesterol synthesis metabolism using fatty acid as a material (cholesterol production controlling ability), an ability of controlling production and consumption of energy (ATP) and an ability of controlling insulin sensitivity are also included in the concept of the obesity improvement effect or onset prevention effect.

Next, the assay method in the present invention will be illustrated. The assay method of the present invention comprises basically (1) a first step of bringing a test substance into contact with a non-human animal of the present invention or a non-human animal and the like of the present invention (namely, non-human animal of the present invention and part thereof), (2) a second step of measuring the expression amount of a human LXRα mutant protein in the non-human animal of the present invention or non-human animal and the like of the present invention (namely, non-human animal of the present invention and part thereof) contacted with the test substance or an index value having a correlation with the expression amount, and comparing the measured amount or value with a control, and (3) a third step of evaluating the anti-obesity ability (for example, the obesity improvement effect or onset prevention effect) of the test substance based on the comparison result in the second step, and more specifically, a first assay method of the present invention and second assay method of the present invention described below, and the like are mentioned.

In the aforementioned assay method, "test substance" is not particularly restricted, and includes nucleic acids, peptides, proteins (including antibody to human LXRα mutant protein), organic compounds, inorganic compounds and the like, and mentioned are cell extracts, expression products of a gene library, synthetic low-molecule organic compounds, synthetic peptides, synthetic nucleic acids, natural compounds and the like.

When a non-human animal of the present invention is used in the above-mentioned assay method, this non-human animal is bred under usual breeding conditions using a standard diet or under breeding conditions giving a high-fat diet. The diet ingesting method is not particularly restricted, and ingestion is freely conducted, or a certain amount of diet is ingested at a certain time. Here, as the standard diet, diets generally used by those skilled in the art appropriately depending on each animal species may be advantageously used. When high-fat diet is imparted, it becomes possible to more effectively induce onset of obesity due to diet by controlling its composition and dieting conditions. Specifically, the fat content of a unit diet component can be selected in a range of 10 to 60 kcal % (standard diet: about 35 kcal %), further, the animal fat content can be controlled at 0.5 to 10-fold based on the vegetable fat content. "High-fat diet ingestion time" means any time during the breeding period under controlled diet conditions for a certain period, and time, period, frequency and quantity are not limited in a period from embryonic period to mortality. Change in pathological conditions can be observed by carrying out fasting temporarily for about 2 to 24 hours during the period, and carrying out a biochemical test. Further preferably, breeding is carried out in separate animal groups of different dieting conditions, and these groups are observed in comparison by time on parameters (body weight, momentum, blood pressure, dieting conditions, biochemical test) regarding a disease associated with usual life behavior and obesity, and then, a histopathological test is carried out. Examples of items in the biochemical test include, but not limited to, blood glucose level, cholesterol level, phospholipid level, triglyceride level, free fatty acid level, insulin level, leptin level, expression amount of an obesity-associated factor, and the like.

In the aforementioned assay method, "bringing a test substance into contact with a non-human animal of the present invention or a non-human animal and the like of the present invention (namely, non-human animal of the present invention or part thereof)" means that a test substance is administered to the non-human animal, or a test substance is brought into contact with a part of the non-human animal, and this can be carried out by methods generally used by those skilled in the art. When a test substance is administered to the non-human animal, the administration method is not particularly restricted, and a test substance may be advantageously administered orally or parenterally. As the parenteral administration method, there are mentioned intravenous administration, subcutaneous administration, intracutaneous administration, intraperitoneal administration (ip), intrarectal administration, percutaneous administration (application) and the like.

The form of a test substance is not particularly restricted, and solid, liquid, mixture with base agent, suspension, solution and the like can be used. In the case of suspension or solution, water, pH buffering solution, methylcellulose solution, physiological saline, organic solvent aqueous solutions (ethanol and dimethyl sulfoxide are usually used as the organic solvent), and the like are used. The base agent includes oils such as glycerin, squalene and the like, and used mainly for preparing a test substance for application.

In the aforementioned assay method, the method for measuring "the expression amount of a human LXRα mutant protein or an index value having a correlation with the expression amount" includes a method of detecting and measuring a gene product (specifically, RNA amount) correlated with the protein, a method of detecting and measuring the expression amount of an obesity-correlated factor described below, and the like. "Index value having a correlation with the expression amount of a human LXRα mutant protein" includes (a) change in body weight in breeding by high-fat diet ingestion;

(b) blood cholesterol level in breeding by high-fat diet ingestion;

(c) visceral fat accumulation amount in breeding by high-fat diet ingestion; and the like, in addition to the above-mentioned values.

Here, "obesity-correlated factors" includes enzymes correlated with glycolysis, gluconeogenesis and glucose incorporation, a factor correlated with control of metabolism, biosynthesis and the like of lipids, a factor correlated with control of cholesterol synthesis and metabolism and energy production and consumption using this as a raw material, and further, a factor correlated with insulin sensitivity in vivo, and specific examples thereof include one or more factors selected from CYP7A1, UCP1, FAS, ACO and the like.

In the case of measuring the expression amount of the obesity-correlated factor, there are mentioned a method of using RNA as a measurement subject and a method of using a protein as a measurement subject.

These will be illustrated in detail below.

(1) In the Case of Use of RNA as Measurement Subject:

In the case of use of RNA as a biological sample, it may be permissible to detect the expression level of a CYP7A1 gene (mouse-derived CYP7A1 gene (Genbank Accession No. NM_007824), human-derived CYP7A1 gene (Genbank Accession No. NM_000780) and the like), UCP1 gene (mouse-derived UCP1 gene (Genbank Accession No. BC012701), human-derived UCP1 gene (Genbank Accession No. U28480) and the like), FAS gene (mouse-derived FAS gene (Genbank Accession No. AF127033), human-derived FAS gene (Genbank Accession No. U29344, U52428) and the like) or ACO gene (mouse-derived ACO gene (Genbank Accession No. AF006688), human-derived ACO gene (Genbank Accession No. AH000843) and the like), per unit amount of total RNA contained in the biological sample, and to measure this, obtaining the expression amount of the obesity-correlated factor.

In the case of use of RNA as a measurement subject after carrying out breeding under load of diet, the onset condition of a disease associated with obesity can be observed by investigating increase and decrease in the expression amount of an obesity-correlated factor gene and change in the expression amount of another gene in conjunction with this by carrying out real-time PCR quantitative analysis or northern blot analysis using, as a material, RNA extracted from each tissue of a non-human animal of the present invention, and eventually, this can be used as an index for elucidating a cause of the disease.

That is, a biological sample originated from a non-human animal of the present invention is brought into contact with a primer or probe originated from an obesity-correlated factor gene, and the amount of RNA to be bound to the primer or probe can be measured by known methods such as a northern blot method, RT-PCR method, DNA chip analysis method, in situ hybridization analysis method and the like. As the primer or probe, a polynucleotide comprising at least continuous 15 bases in a nucleotide sequence of an obesity-correlated factor gene and/or its complementary polynucleotide are mentioned. In the case of use as a primer, those having a base length of usually 15 bp to 100 bp, preferably 15 bp to 50 bp, more preferably 15 bp to 35 bp are exemplified. In the case of use as a detection probe, those having a base length of usually 15 bp to whole sequence, preferably 15 bp to 1 kb, more preferably 100 bp to 1 kb are exemplified.

(a) In the case of use of a northern blot method, specifically, the above-mentioned probe is labeled with a radioactive isotope (RI)($^{32}$P, $^{33}$P and the like), fluorescent substance and the like, and the labeled probe is hybridized with RNA originated from a biological tissue of a test animal transferred to a nylon membrane and the like according to a conventional method. The formed double strand composed of a primer originated from an obesity-correlated factor (DNA or RNA) and total RNA originated from a biological sample is measured by detecting a signal originated from the above-mentioned primer label (RI or fluorescent substance) by a radiation detector (BAS2000, manufactured by Fuji Photo Film Co., Ltd.) or a fluorescence detector. It is also possible that a probe DNA is labeled using Alk Phos Direct Labelling and Detection System (manufactured by Amersham Pharmacia Biotech) according to the protocol, hybridized with RNA originated from a biological sample, then, a signal originated from the probe label is detected and measured by Multi Bio Imager TYPHOON (manufactured by Amersham Pharmacia Biotech).

(b) In the case of use of a RT-PCR method, for example, RNA originated from a biological sample and the above-mentioned primer are hybridized, a PCR method is carried out according to a conventional method, and the resulting amplified double-strand DNA is detected. For detection of the amplified double-stranded DNA, a method of detecting labeled double-stranded DNA produced by effecting the above-mentioned PCR using a primer previously labeled by RI or fluorescent substance, a method of transferring the produced double-stranded DNA to a nylon membrane and the like according to a conventional method, using a labeled disease marker as a probe and hybridizing the marker with this DNA, and detecting the DNA, and the like, can be used. Besides, it is also possible to prepare a RT-PCR reaction solution with SYBR Green RT-PCR Reagents (manufactured by Applied Biosystems) according to the protocol, react this by ABI PRIME 7900 Sequence Detection System (manufactured by Applied Biosystems), and detect the reaction product.

(c) In the case of use of DNA chip analysis, for example, a DNA chip to which the above-mentioned primer or probe has been immobilized as a DNA probe (single strand or double strand) is prepared. To this is hybridized cRNA prepared from RNA originated from a biological tissue according to a conventional method. The formed double strand composed of DNA and cRNA is bound to a labeled probe prepared from the above-mentioned primer or probe, and detected. As the above-mentioned DNA chip, a DNA chip capable of detecting and measuring the gene expression level of a CYP7A1 gene, UCP1 gene, ACO gene or FAS gene can also be used.

(2) In the Case of Use of Protein as Measurement Subject:

In the case of use of a solution containing a protein as a biological sample, an obesity-correlated factor contained in the biological sample is reacted with an antibody capable of recognizing the obesity-correlated factor, thereby, the amount of the obesity-correlated factor capable of binding to the antibody is detected and measured. The animal species from which the antibody capable of recognizing the obesity-correlated factor is originated is not particularly restricted, and usually, an antibody produced by using an antigen originated from the same species as the non-human animal of the present invention is used. The obesity-correlated factor includes specifically CYP7A1, UCP1, FAS and ACO, and as its amino acid sequence, amino acid sequence of proteins encoded by the above-mentioned obesity-correlated factor genes respectively are mentioned.

"Control" in the above-mentioned assay method means, for example, (i) the case of carrying out the same step as in the first conventional and second conventional, using as a subject a wild-type non-human animal which is the same animal species as the non-human animal of the present invention used in the assay method, or (ii) the case of carrying out the same conventional as in the first conventional and second conventional, using a control substance (positive control, negative control) instead of test substance, or the like.

In the aforementioned case (i), if the obesity improvement effect or onset prevention effect in the non-human animal of the present invention is equivalent to or more than the obesity improvement effect or onset prevention effect of a test substance in a wild-type non-human animal, this test substance can be evaluated to have an obesity improvement effect or onset prevention effect. On the otherhand, if the obesity improvement effect or onset prevention effect in the non-human animal of the present invention is smaller than the obesity improvement effect or onset prevention effect of a test substance in a wild-type non-human animal, this test substance can be evaluated to have no obesity improvement effect or onset prevention effect ascribable to a human LXRα mutant.

In the above-mentioned case (ii), a positive control or negative control is mentioned as the control substance. The positive control means any substance having an obesity improvement effect or onset prevention effect, and specifically, corticosteroid and the like are exemplified. As the negative control, a solvent contained in a test substance, a test solution as a back ground, and the like, are mentioned.

In the case of use of the control substance as a negative control, if the obesity improvement effect or onset prevention effect in the non-human animal of the present invention is larger than the obesity improvement effect or onset prevention effect of a control substance, this test substance can be evaluated to have an obesity improvement effect or onset prevention effect. On the other hand, if the obesity improvement effect or onset prevention effect of a test substance is equivalent to or smaller than the obesity improvement effect or onset prevention effect of a control substance, this test substance can be evaluated to have no obesity improvement effect or onset prevention effect.

In the case of use of the control substance as a positive control, the obesity improvement effect or onset prevention effect of a test substance and the obesity improvement effect or onset prevention effect of a control substance can be compared, thereby, evaluating the extent of the obesity improvement effect or onset prevention effect of the test substance.

The first assay method of the present invention is an assay method for the anti-obesity ability of a substance characterized by comprising bringing a test substance into contact with a non-human animal of the present invention (namely, contact step), measuring the presence or absence of variation in the blood cholesterol level of the non-human animal or its extent (namely, measurement step), and evaluating the anti-obesity ability of the test substance based on the measured result (namely, evaluation step).

For measurement of blood cholesterol level in the measurement step, a method by an enzymatic immune adsorption analysis method kit (Roche Dianostics) conventionally used in the art, and the like may be used.

The second assay method of the present invention is an assay method for the anti-obesity ability of a substance characterized by comprising bringing a test substance into contact with a non-human animal of the present invention (namely, contact step), measuring the presence or absence of variation in the expression amount of a liver X receptor α mutant protein having at least an amino acid sequence encoded by exon 5 of a liver X receptor α gene in the non-human animal and the like contacted with the above-mentioned test substance or an index value having a correlation with the expression amount or the extent of the variation (namely, measurement step), and evaluating the anti-obesity ability of the test substance based on the measured result (namely, evaluation step).

When the non-human animal and the like of the present invention is a part of a non-human animal or its progeny (namely, tissue or cell originated from the non-human animal), the concentration of a ligand or test substance to be contacted with a part of the animal is, in usual, advantageously from about 0.1 µM to about 10 µM, preferably from 1 µM to 10 µM. The contact time of a part of the animal with a ligand or test substance is usually 18 hours or more and about 60 hours, and preferably from about 24 to 40 hours.

When the index value having a correlation with the expression amount of a liver X receptor α mutant protein having at least an amino acid sequence encoded by exon 5 of a liver X receptor α gene in the non-human animal and the like contacted with the above-mentioned test substance is a value of, for example, blood glucose level, glucose tolerance, blood cholesterol level, liver triglyceride amount and the like, a measurement method as described later may be advantageously used.

As the method of measuring blood glucose level, a maximum reaction acceleration method (Glucoroder-NX K.K.

A&T) using a glucose oxidation enzyme immobilized enzyme electrode conventionally used in the art, and the like may be used.

As the method of measuring glucose tolerance, OGTT (oral glucose tolerance test) and ITT (insulin tolerance test) and the like are mentioned. Preferably, area under the curve (AUC) is calculated from the result, and its increase can be used as an index for lowering of glucose tolerance.

As the method of measuring blood cholesterol level, a method by an enzymatic immune adsorption analysis method kit (Roche Dianostics) conventionally used in the art, and the like may be used.

As the method of measuring liver triglyceride amount, an acetylacetone method (method described in Fletcher, M. J.: Clin. Chim. Acta, 22, 339-397 (1968) and Sardesai, V. M.: Clin. Chim. Acta, 14, 156-161 (1968)) conventionally used in the art, and the like may be used.

Other methods of biochemically analyzing a transgenic non-human animal of the present invention may be conducted according to known methods usually used in the art.

Furthermore, the assay method of the present invention may be, for example, an assay method in which a step of bringing a ligand of the present LXRα mutant protein into contact with a non-human animal of the present invention or a non-human animal and the like of the present invention (namely, non-human animal of the present invention or part thereof) is further added as the simultaneous step or previous step of the first step of bringing a test substance into contact with a non-human animal of the present invention or a non-human animal and the like of the present invention (namely, non-human animal of the present invention or part thereof). In this assay method, it is also possible to evaluate an antagonistic activity of a test substance against the ligand. An agent comprising as an active ingredient a test substance having an antagonistic activity against the ligand selected based on the antagonistic activity evaluated by the assay may be advantageously used according to the same administration method, preparation method, dose and the like as in explanations regarding the anti-obesity agent of the present invention described later.

The searching method of the present invention is a method for searching a substance having an anti-obesity ability characterized by selecting a test substance having an anti-obesity ability based on the anti-obesity ability evaluated by the first assay method of the present invention or the second assay method of the present invention. Thus selected substance having an anti-obesity ability may be used as an active ingredient of the anti-obesity agent of the present invention.

The substance selected by the searching method of the present invention may form a salt, and as the salt of this substance, salts with physiologically acceptable acids (e.g., inorganic acids, organic acids) or metals (e.g., alkali metals) are used, and particularly, physiologically acceptable acid addition salts are preferable. As such salts, for example, salts with inorganic acids (e.g., hydrochloric acid, phosphoric acid, hydrobromic acid, sulfuric acid), or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid), and the like are used. The substance selected by the searching method of the present invention can be used, for example, orally in the form of tablet if necessary coated with sugar, capsule, elixir, microcapsule and the like, or parenterally in the form of an injectable solution such as a sterile solution with water or other pharmaceutically acceptable liquid, suspension and the like. For example, this substance can be mixed with a physiologically acceptable carrier, flavor, excipient, vehicle, preservative, stabilizer, binder and the like in the form of unit dose required for execution of generally accepted preparation, to produce a preparation. The amount of an active ingredient in these preparations is so selected that a suitable volume in an indicated range is obtained. As the additive which can be mixed in tablet, capsule and the like, there can be used, for example, binders such as gelatin, corn starch, tragacanth and gum Arabic, excipients such as crystalline cellulose, swelling agents such as corn starch, gelatin, alginic acid and the like, lubricants such as magnesium stearate, sweeteners such as sucrose, lactose or saccharin, spices such as peppermint, lean meat oil or cherry, and the like. When the dispensing unit form is capsule, the above-mentioned type material can further contain a liquid carrier such as fat and oil. The sterile composition for injection can be formulated according to usual preparation procedures such as dissolving or suspending of active substances in vehicle such as injection water, and naturally produced vegetable oils and the like such as sesame oil, coconut oil and the like. As the aqueous solution for injection, for example, physiological saline, glucose, and isotonic solution containing other adjuvants (e.g.,D-sorbitol, D-mannitol, sodium chloride, etc.) and the like are used, and may be used together with a suitable solution auxiliary, for example, alcohol (e.g., ethanol), polyalcohol (e.g., propylene glycol, polyethylene glycol), nonionic surfactant (e.g., polysorbate 80, HCO-50) and the like. As the oily liquid, for example, sesame oil, soybean oil and the like are used, and it may be used together with a solution auxiliary, benzyl benzoate, benzyl alcohol and the like. In the above-mentioned therapeutic and onset prevention agents, for example, buffering agents (e.g., phosphate buffering solution, sodium acetate buffering solution), soothing agents (e.g., benzalconium chloride, procaine hydrochloride and the like), stabilizers (e.g., human serum albumin, polyethylene glycol and the like), preservatives (e.g., benzyl alcohol, phenol and the like), antioxidants and the like may be compounded. The prepared medicinal composition such as injectable solution and the like is usually filled in a suitable ample.

Thus obtained preparation can, because of safeness and low toxicity, be administered to human and mammal animals (e.g., rat, rabbit, sheep, pig, cow, cat, dog, monkey and the like). The dose of the substance varies depending on the administration subject (e.g., animal species, age, sex, body weight), subject disease, administration route and the like, and when this compound is administered orally, the dose of this substance is about 1 mg to about 2 g, preferably about 1 mg to about 1 g, more preferably about 5 mg to about 50 mg per day, in a general adult (body weight is hypothesized to 60 kg). When administered parenterally, the once dose of this substance varies depending on administration subject, subject disease and the like, and for example, when this substance is administered in the form of injection to a usual adult (hypothesized to 60 kg), it is convenient to administer this substance by intravenous injection in an amount of about 0.01 mg to about 500 mg, preferably about 0.1 mg to about 50 mg, more preferably about 0.1 mg to about 10 mg per day. Also in the case of other non-human animal, an amount converted per 60 kg can be administered.

EXAMPLES

The following examples will illustrate the present invention further in detail, but the invention is not limited to them. Specific operations described below were carried out according to methods conventionally used in the art described in, for example, Molecular Cloning, vol. 3: A Laboratory Manual, Cold Spring Harbor Laboratory, Clod Spring Harbor, N.Y. (2001), Hong, B.L.M., A Laboratory Manual, Cold Spring Harbor Laboratory Press, Clod Spring Harbor, N.Y. (1986) and the like, unless otherwise stated.

Example 1

Production of Nucleic Acid Construct for Producing Transgenic Mouse pALBe/p-hLXRα5A-SV40 PolyA was produced (see, FIG. 1) by inserting DNA encoding a translation region of human LXRα mutant 5A by ligation into a XbaI site present between a region comprising a promoter of a mouse-derived albumin gene and an enhancer element for said promoter, and a SV40PolyA sequence (Shiota et al., Proc. Natl. Acad. Sci. U.S.A. 1992, 89, 373-377). The produced pALBe/p-hLXRα5A-SV40PolyA was digested with a restriction enzyme AatII and MluI (37° C., 1 hour). The digested product was fractionated by electrophoresis using 1% agarose gel. The fractionated intended DNA band was cut from the above-mentioned agarose gel, then, this DNA was extracted by phenol, to obtain a supernatant fraction containing the DNA. The resultant supernatant fraction was further precipitated by ethanol, to recover a nucleic acid construct as the intended DNA.

Example 2

Production of Transgenic Mouse (1) Collection of Mouse Fertilized Ovum Used for Transfer of Nucleic Acid Construct of the Present Invention For inducing excess ovulation in a female mouse of B6C3F1 mouse, reproductive organs from ovary to uterus were taken from an individual to which 5 international units of pregnant mare's serum gonadotropin (Serotopin, manufactured by Teikoku Hormone Mfg Co., Ltd.) and 2.5 international units of human chorionic gonadotropin (Gonadotropin, manufactured by Teikoku Hormone Mfg Co., Ltd.) had been previously administered intraperitoneally, and an oviduct was torn under a stereo microscope, and a fertilized ovum was collected from the oviduct. An M2 medium was used as a medium for culturing a mouse ovum.

(2) Injection of Linearized DNA into Mouse Fertilized Ovum Male Pronucleus (Microinjection) and Culturing of Mouse Ovum Comprising this DNA (hereinafter, Referred to as Manipulated Ovum)

The pALBe/p-hLXRα5A-SV40PolyA recovered in Example 1 was linearized by a restriction enzyme. The pALBe/p-hLXRα5A-SV40PolyA was micro-injected into the above-mentioned fertilized ovum using a micro manipulator (suspending type joy stick three-dimensional oil pressure micro manipulator is installed to coarse adjustment electrically powered manipulator: manufactured by Narishige), micro injector (manufactured by Narishige), injection pipet and holding pipet under an inverted microscope equipped with a Nomarski differential interference apparatus (inverted type system microscope: manufactured by Olympus), to prepare a manipulated ovum. Regarding a dish for injection, a drop of medium 50 µl was made on a 10 cm dish (Falcon 3002: manufactured by Becton Dickinson) and liquid paraffin was laminated. This was allowed to stand still in an incubator of 37° C. for 30 minutes or more in the presence of 5% $CO_2$. Further, the manipulated ovum was transferred into the M2 medium drop using a glass capillary under a stereomicroscope. This manipulated ovum was allowed to stand still in an incubator of 37° C. in the presence of 5% $CO_2$ until transferring into a mouse oviduct.

(3) Production of Pseudopregnant Mouse by Mating of Spermatic Duct-Ligated Male Mouse and Normal Female Mouse, Tansplantation of Manipulated Ovum into this Pseudopregnant Mouse, and Birth of Pseudopregnant Mouse and Growth of Born Child For pseudopregnancy of an ICR mouse normal female, mating with a supermatic duct-ligated male mouse was carried out.

For transplantion of the manipulated ovum prepared in the above-mentioned item (2) into a pseudopregnant ICR mouse, first, the mouse was subjected to general anesthesia using 50 mg/body weight of pentobarbital sodium (Nenbutal: Abbott Laboratories). Then, both cord parts of the mouse were cut by about 1 cm to expose ovary and oviduct, further, ovarian bursa was dissected by tweezers under a stereomicroscope, to expose fimbriae of oviduct. Then, 10 to 15 the above-mentioned manipulated ova per oviduct were transferred into fimbriae of oviduct. Then, oviduct and ovary were retuned into an abdominal cavity and both the cut parts were sutured, then, the mouse was awoken from anesthesia. Thus prepared female mouse was allowed to give birth, to obtain a child mouse (transgenic mouse).

Example 3

Detection of Transferred Nucleic Acid Construct of the Present Invention

The presence of the transferred nucleic acid construct in the child mouse obtained in Example 2 was confirmed by amplifying and detecting this nucleic acid construct by PCR using, as a template, DNA extracted from a tail of the child mouse.

First, a part of the tail of the child mouse was immersed in a solution buffer (100 mM Tris-HCl (pH 7.5), 5 mM EDTA, 200 mM NaCl, 0.2% SDS, 0.1 mg/ml Proteinase K), and heated at 55° C. for 6 hours. Then, this mixture was centrifuged, the residue was removed, then, the supernatant fraction was extracted by phenol-chloroform, to obtain a supernatant fraction from which proteins had been removed. The resultant supernatant fraction was further precipitated by ethanol, to recover DNA.

For confirming transfer of a nucleic acid construct for producing transgenic mouse (a transgene), a PCR method was used. This PCR method was carried out using a programmable thermal cycler.

Fifty (50) µl of the reaction solution contains 1.25 units of ExTaq DNA polymerase (manufactured by Takara Bio) and each 200 nmol of sense primer (SEQ ID No: 9) and antisense primer (SEQ ID No: 10), and the DNA prepared from a tail of the mouse as described above. Regarding the reaction conditions of the PCR method, the reaction solution was heat-denaturated at 95° C. for 3 minutes, then, was subjected to a reaction of 35 cycles, one cycle being at 94° C. for 30 seconds, at 55° C. for 30 seconds and at 74° C. for 60 seconds. Then, a PCR product amplified by this PCR method was subjected to electrophoresis using 1% agarose gel, to confirm amplification of DNA based on the above-mentioned nucleic acid construct.

Example 4

Increase in Body Weight in Transgenic Mouse by Ingestion of High-Fat Diet

Figure 2:
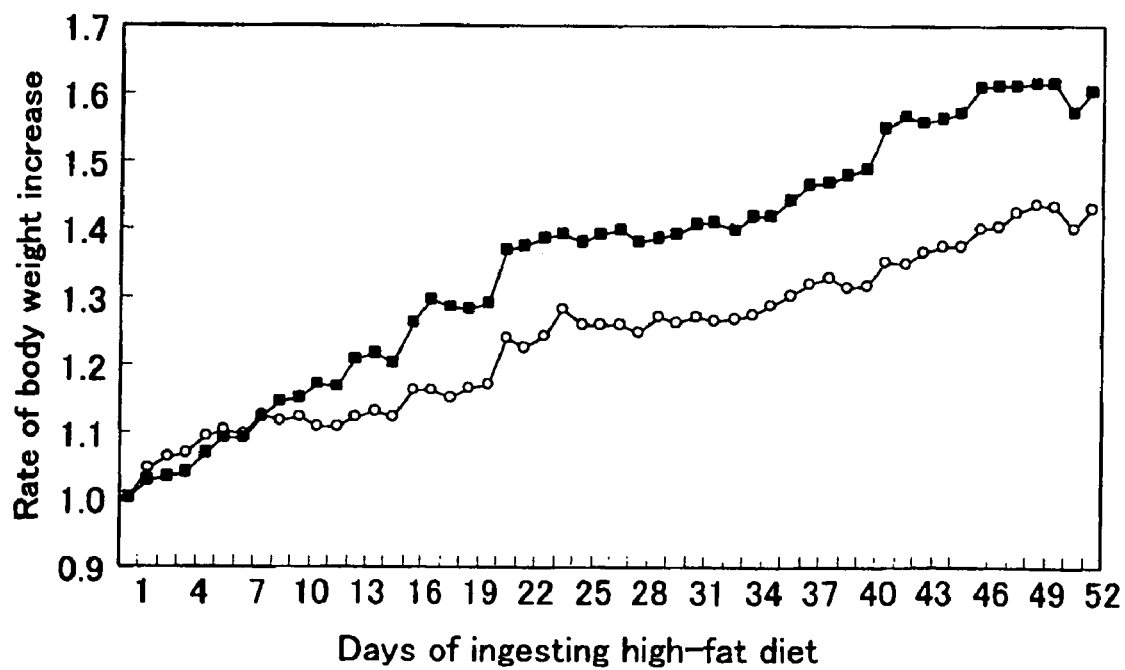
FIG. 2 is a view showing change in body weight when wild-type mice and transgenic mice (both 8-week old, female, n=3) were allowed to ingest a high-fat diet for two months. Open circles represent result of wild-type mice and black squareas represent result of transgenic mice.

The child mouse obtained in Example 2 and allowed to ingest a high-fat diet showed remarkably high increase in body weight as compared with a wild-type mouse which ingested a high-fat diet likewise, and its difference is about 20% (see, FIG. 2).

Example 5

Figure 3:
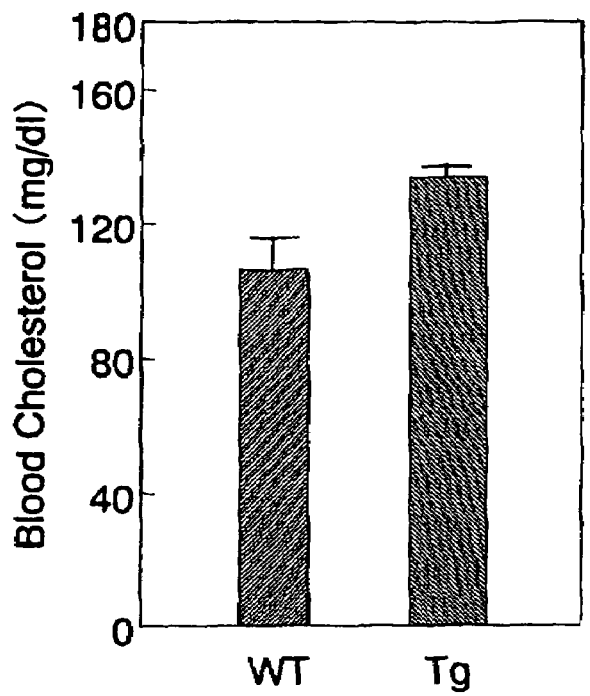
FIG. 3 is a view showing results of measurement of blood cholesterol level after wild-type mice (WT) and transgenic mice (Tg) (both 8-week old, female, n=3) were allowed to ingest a high-fat diet for two months.

Measurement of Blood Cholesterol Level in Transgenic Mouse by Ingestion of High-Fat Diet The blood cholesterol level in the child mouse obtained in Example 2 was measured by a cholesterol oxidase-HMMPS method using a commercially available kit (Wako Pure Chemical Industries, Ltd.). As a result, transgenic mice (litter female) (n=3) which ingested a high-fat diet showed remarkably high blood cholesterol level as compared with 16-week old wild-type females (n=3) which ingested a high-fat diet likewise, and its difference is about 30% (see, FIG. 3).

Example 6

Analysis of Expression of Various Genes in Transgenic Mouse

Extraction of RNA from each liver of both wild-type mice and transgenic mice was carried out using a commercially available TRIZOL reagent (manufactured by Invitrogen) according to a protocol appended to the reagent. Using the extracted total RNA as a template, an oligo dT primer or random primer and a reverse transcriptase (RNaseH-Superscript II Reverse Transcriptase (manufactured by Invitrogen)) were reacted at 42° C. for 1 hour, then, the reaction mixture was heated at 99° C. for 5 minutes to deactivate the reverse transcriptase, synthesizing cDNA.

Next, using the synthesized cDNA as a template, the expression amounts of various genes were quantified by a real-time PCR method. The real-time PCR was carried out using Universal PCR Master Mix (Applied BioSystems) according to a protocol appended to the kit. Each 50 pmol of primer sets for specific amplification, and a TaqMan probe, exogenously transferred human LXRα mutant 5A genes (SEQ ID NOs: 11, 12 and 13), CYP7A1 genes (SEQ ID NOs: 14, 15 and 16), and 1 µl of cDNA synthesized as described above, were used, and real-time PCR was performed. Also, using the same template cDNA, the mRNA amount of G3PDH was measured.

Figure 4:
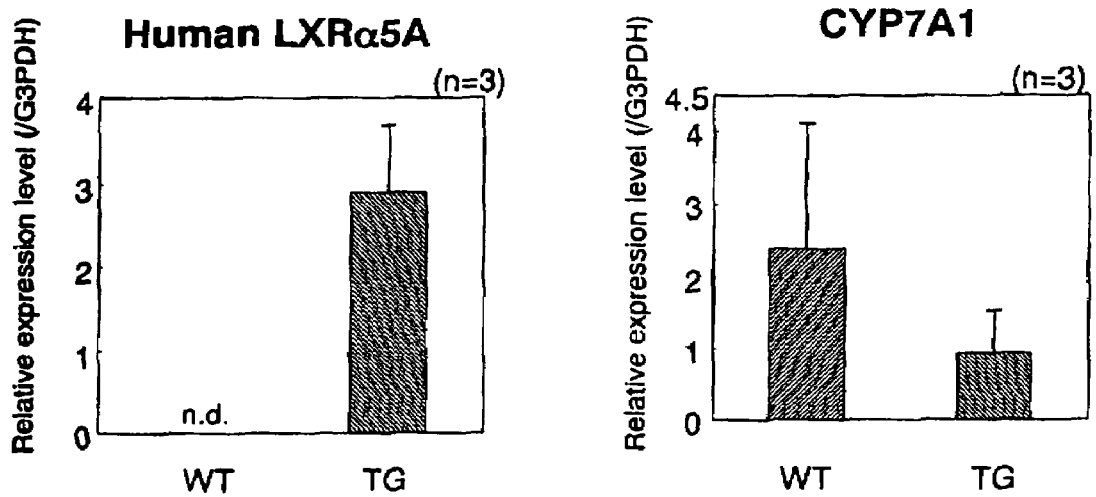
FIG. 4 is a view showing results of the expression analysis of a human LXRα mutant 5A gene and mouse CYP7A1 gene in liver after wild-type mice (WT) and transgenic mice (TG) (both 8-week old, female, n=3) were allowed to ingest a high-fat diet for two months.

As apparent from FIG. 4, expression of a human LXRα mutant 5A gene was confirmed only in liver of the transgenic mouse. On the other hand, expression of a CYP7A1 gene (target gene of LXRα) as a rate controlling enzyme in a cholesterol metabolism pathway decreased significantly in liver of the transgenic mouse as compared with a wild-type mouse. From these result, it was clarified that a human LXRα mutant 5A protein suppresses the function of LXRα in liver, and lowers a cholesterol metabolism ability.

What is claimed is:

1. A transgenic mouse or its progeny or part thereof, which comprises in its genome a nucleic acid construct comprising a polynucleotide encoding an isoform of human-derived liver X receptor α protein that comprises the amino acid sequence of SEQ ID NO: 1:

wherein a liver-specific promoter is operably linked to the polynucleotide; and wherein the LXRα protein is expressed in liver; and wherein the mouse exhibits an increase in body weight and blood cholesterol compared to a wild-type mouse, after ingestion of a high-fat diet.

2. A transgenic mouse or its progeny, which comprises in its genome a nucleic acid construct comprising a polynucleotide encoding an isoform of human-derived liver X receptor α protein that comprises the amino acid sequence of SEQ ID NO: 1:

wherein a liver-specific promoter is operably linked to the polynucleotide; and wherein the LXRα protein is expressed in liver; and wherein the mouse exhibits an increase in body weight and blood cholesterol compared to a wild-type mouse, after ingestion of a high-fat diet.

3. The transgenic mouse or its progeny or part thereof according to claim 1, wherein the polynucleotide is operably linked further to an enhancer element for the promoter.

4. The transgenic mouse or its progeny or part thereof according to claim 3, wherein the promoter is a promoter of a mouse albumin gene.

* * * * *

SEQUENCE LISTING

```
<160> NUMBER OF SEQ ID NOS: 16

<210> SEQ ID NO 1
<211> LENGTH: 511
<212> TYPE: PRT
<213> ORGANISM: Homo sapiens

<400> SEQUENCE: 1

Met Ser Leu Trp Leu Gly Ala Pro Val Pro Asp Ile Pro Pro Asp Ser
  1               5                  10                  15

Ala Val Glu Leu Trp Lys Pro Gly Ala Gln Asp Ala Ser Ser Gln Ala
             20                  25                  30

Gln Gly Gly Ser Ser Cys Ile Leu Arg Glu Glu Ala Arg Met Pro His
         35                  40                  45

Ser Ala Gly Gly Thr Ala Gly Val Gly Leu Glu Ala Ala Glu Pro Thr
     50                  55                  60

Ala Leu Leu Thr Arg Ala Glu Pro Pro Ser Glu Pro Thr Glu Ile Arg
 65                  70                  75                  80

Pro Gln Lys Arg Lys Lys Gly Pro Ala Pro Lys Met Leu Gly Asn Glu
                 85                  90                  95

Leu Cys Ser Val Cys Gly Asp Lys Ala Ser Gly Phe His Tyr Asn Val
            100                 105                 110

Leu Ser Cys Glu Gly Cys Lys Gly Phe Phe Arg Arg Ser Val Ile Lys
        115                 120                 125

Gly Ala His Tyr Ile Cys His Ser Gly Gly His Cys Pro Met Asp Thr
    130                 135                 140

Tyr Met Arg Arg Lys Cys Gln Glu Cys Arg Leu Arg Lys Cys Arg Gln
145                 150                 155                 160

Ala Gly Met Arg Glu Glu Cys Val Leu Ser Glu Glu Gln Ile Arg Leu
                165                 170                 175

Lys Lys Leu Lys Arg Gln Glu Glu Glu Gln Ala His Ala Thr Ser Leu
```

-continued

```
                180                 185                 190
Pro Pro Arg Arg Ser Ser Pro Pro Gln Ile Leu Pro Gln Leu Ser Pro
            195                 200                 205

Glu Gln Leu Gly Met Ile Glu Lys Leu Val Ala Ala Gln Gln Gln Cys
        210                 215                 220

Asn Arg Arg Ser Phe Ser Asp Arg Leu Arg Val Thr Pro Trp Pro Met
225                 230                 235                 240

Ala Pro Asp Pro His Ser Arg Glu Ala Arg Gln Gln Arg Phe Ala His
                245                 250                 255

Phe Thr Glu Leu Ala Ile Val Ser Val Gln Glu Ile Val Asp Phe Ala
            260                 265                 270

Lys Gln Leu Pro Gly Phe Leu Gln Leu Ser Arg Glu Asp Gln Ile Ala
        275                 280                 285

Leu Leu Lys Thr Ser Ala Ile Glu Val Ala Gly Glu Gly Gln Gly Met
        290                 295                 300

Lys Gly Glu Ala Glu Trp Asp Tyr Leu Trp Gly Pro Pro Asp Ile
305                 310                 315                 320

Glu Leu Gly Glu Pro Asn Leu Leu Gly Ser Arg Asp Glu Glu Asn Arg
                325                 330                 335

Pro Pro Trp Lys Arg Pro Cys Ser Lys Thr Ser Pro Ser Pro Arg
            340                 345                 350

Leu Arg Phe Ala Ala Cys Val Gln Val Met Leu Leu Glu Thr Ser Arg
        355                 360                 365

Arg Tyr Asn Pro Gly Ser Glu Ser Ile Thr Phe Leu Lys Asp Phe Ser
        370                 375                 380

Tyr Asn Arg Glu Asp Phe Ala Lys Ala Gly Leu Gln Val Glu Phe Ile
385                 390                 395                 400

Asn Pro Ile Phe Glu Phe Ser Arg Ala Met Asn Glu Leu Gln Leu Asn
                405                 410                 415

Asp Ala Glu Phe Ala Leu Leu Ile Ala Ile Ser Ile Phe Ser Ala Asp
            420                 425                 430

Arg Pro Asn Val Gln Asp Gln Leu Gln Val Glu Arg Leu Gln His Thr
        435                 440                 445

Tyr Val Glu Ala Leu His Ala Tyr Val Ser Ile His His Pro His Asp
    450                 455                 460

Arg Leu Met Phe Pro Arg Met Leu Met Lys Leu Val Ser Leu Arg Thr
465                 470                 475                 480

Leu Ser Ser Val His Ser Glu Gln Val Phe Ala Leu Arg Leu Gln Asp
                485                 490                 495

Lys Lys Leu Pro Pro Leu Leu Ser Glu Ile Trp Asp Val His Glu
            500                 505                 510

<210> SEQ ID NO 2
<211> LENGTH: 356
<212> TYPE: PRT
<213> ORGANISM: Homo sapiens

<400> SEQUENCE: 2

Met Ser Leu Trp Leu Gly Ala Pro Val Pro Asp Ile Pro Pro Asp Ser
1               5                   10                  15

Ala Val Glu Leu Trp Lys Pro Gly Ala Gln Asp Ala Ser Ser Gln Ala
            20                  25                  30

Gln Gly Gly Ser Ser Cys Ile Leu Arg Glu Glu Ala Arg Met Pro His
        35                  40                  45
```

```
Ser Ala Gly Gly Thr Ala Gly Val Gly Leu Glu Ala Ala Glu Pro Thr
    50                  55                  60
Ala Leu Leu Thr Arg Ala Glu Pro Pro Ser Glu Pro Thr Glu Ile Arg
 65                  70                  75                  80
Pro Gln Lys Arg Lys Gly Pro Ala Pro Lys Met Leu Gly Asn Glu
                 85                  90                  95
Leu Cys Ser Val Cys Gly Asp Lys Ala Ser Gly Phe His Tyr Asn Val
                100                 105                 110
Leu Ser Cys Glu Gly Cys Lys Gly Phe Phe Arg Arg Ser Val Ile Lys
                115                 120                 125
Gly Ala His Tyr Ile Cys His Ser Gly Gly His Cys Pro Met Asp Thr
130                 135                 140
Tyr Met Arg Arg Lys Cys Gln Glu Cys Arg Leu Arg Lys Cys Arg Gln
145                 150                 155                 160
Ala Gly Met Arg Glu Glu Cys Val Leu Ser Glu Glu Gln Ile Arg Leu
                165                 170                 175
Lys Lys Leu Lys Arg Gln Glu Glu Glu Gln Ala His Ala Thr Ser Leu
                180                 185                 190
Pro Pro Arg Arg Ser Ser Pro Pro Gln Ile Leu Pro Gln Leu Ser Pro
                195                 200                 205
Glu Gln Leu Gly Met Ile Glu Lys Leu Val Ala Ala Gln Gln Gln Cys
210                 215                 220
Asn Arg Arg Ser Phe Ser Asp Arg Leu Arg Val Thr Pro Trp Pro Met
225                 230                 235                 240
Ala Pro Asp Pro His Ser Arg Glu Ala Arg Gln Gln Arg Phe Ala His
                245                 250                 255
Phe Thr Glu Leu Ala Ile Val Ser Val Gln Glu Ile Val Asp Phe Ala
                260                 265                 270
Lys Gln Leu Pro Gly Phe Leu Gln Leu Ser Arg Glu Asp Gln Ile Ala
                275                 280                 285
Leu Leu Lys Thr Ser Ala Ile Glu Val Met Leu Leu Glu Thr Ser Arg
                290                 295                 300
Arg Tyr Asn Pro Gly Ser Glu Ser Ile Thr Phe Leu Lys Asp Phe Ser
305                 310                 315                 320
Tyr Asn Arg Glu Asp Phe Ala Lys Ala Gly Ser Arg Ser Val Ala Gln
                325                 330                 335
Ala Glu Cys Ser Gly Val Ile Asn His Gly Ser Met Gln Pro Arg Pro
                340                 345                 350
Ser Gly Leu Lys
        355

<210> SEQ ID NO 3
<211> LENGTH: 1536
<212> TYPE: DNA
<213> ORGANISM: Homo sapiens

<400> SEQUENCE: 3
atgtccttgt ggctgggggc ccctgtgcct gacattcctc ctgactctgc ggtggagctg      60
tggaagccag gcgcacagga tgcaagcagc caggcccagg gaggcagcag ctgcatcctc     120
agagaggaag ccaggatgcc ccactctgct gggggtactg caggggtggg gctggaggct     180
gcagagccca cagccctgct caccagggca gagccccctt cagaacccac agagatccgt     240
ccacaaaagc ggaaaaaggg gccagccccc aaaatgctgg ggaacgagct atgcagcgtg     300
tgtggggaca aggcctcggg cttccactac aatgttctga gctgcgaggg ctgcaaggga     360
```

```
ttcttccgcc gcagcgtcat caagggagcg cactacatct gccacagtgg cggccactgc    420
cccatggaca cctacatgcg tcgcaagtgc caggagtgtc ggcttcgcaa atgccgtcag    480
gctggcatgc gggaggagtg tgtcctgtca aagaacaga tccgcctgaa gaaactgaag     540
cggcaagagg aggaacaggc tcatgccaca tccttgcccc ccaggcgttc ctcaccccc     600 caaatcctgc cccagctcag cccggaacaa ctgggcatga tcgagaagct cgtcgctgcc    660
cagcaacagt gtaaccggcg ctccttttct gaccggcttc gagtcacgcc ttggcccatg    720
gcaccagatc cccatagccg ggaggcccgt cagcagcgct tgcccactt cactgagctg     780 gccatcgtct ctgtgcagga gatagttgac tttgctaaac agctaccgg cttcctgcag     840 ctcagccggg aggaccagat tgccctgctg aagacctctg cgatcgaggt ggctggagaa    900
gggcaaggga tgaagggaga agcagagtgg gattatctgt gggagggggcc tccagacatc   960 gagctgggag agccaaatct gctgggaagc agggatgagg agaatcggcc tccctggaag   1020
aggccatgct ccaagaccag ccctcctagt ccccgtttga ggtttgctgc ttgtgtgcag  1080
gtgatgcttc tggagacatc tcggaggtac aaccctggga gtgagagtat caccttcctc  1140
aaggatttca gttataaccg ggaagacttt gccaaagcag ggctgcaagt ggaattcatc  1200
aaccccatct tcgagttctc cagggccatg aatgagctgc aactcaatga tgccgagttt  1260
gccttgctca ttgctatcag catcttctct gcagaccggc ccaacgtgca ggaccagctc  1320
caggtggaga ggctgcagca cacatatgtg gaagccctgc atgcctacgt ctccatccac  1380
catccccatg accgactgat gttcccacgg atgctaatga aactggtgag cctccggacc  1440
ctgagcagcg tccactcaga gcaagtgttt gcactgcgtc tgcaggacaa aaagctccca  1500
ccgctgctct ctgagatctg ggatgtgcac gaatga                             1536

<210> SEQ ID NO 4
<211> LENGTH: 1453
<212> TYPE: DNA
<213> ORGANISM: Homo sapiens

<400> SEQUENCE: 4
atgtccttgt ggctgggggc ccctgtgcct gacattcctc ctgactctgc ggtggagctg     60
tggaagccag gcgcacagga tgcaagcagc caggcccagg gaggcagcag ctgcatcctc    120
agagaggaag ccaggatgcc ccactctgct gggggtactg caggggtggg gctggaggct    180
gcagagccca cagccctgct caccagggca gagccccctt cagaacccac agagatccgt    240
ccacaaaagc ggaaaaaggg gccagccccc aaaatgctgg ggaacgagct atgcagcgtg    300 tgtgggggaca aggcctcggg cttccactac aatgttctga gctgcgaggg ctgcaaggga   360
ttcttccgcc gcagcgtcat caagggagcg cactacatct gccacagtgg cggccactgc   420
cccatggaca cctacatgcg tcgcaagtgc caggagtgtc ggcttcgcaa atgccgtcag   480
gctggcatgc gggaggagtg tgtcctgtca aagaacaga tccgcctgaa gaaactgaag    540
cggcaagagg aggaacaggc tcatgccaca tccttgcccc ccaggcgttc ctcaccccc    600 caaatcctgc cccagctcag cccggaacaa ctgggcatga tcgagaagct cgtcgctgcc   660
cagcaacagt gtaaccggcg ctccttttct gaccggcttc gagtcacgcc ttggcccatg   720
gcaccagatc cccatagccg ggaggcccgt cagcagcgct tgcccactt cactgagctg    780 gccatcgtct ctgtgcagga gatagttgac tttgctaaac agctaccgg cttcctgcag    840 ctcagccggg aggaccagat tgccctgctg aagacctctg cgatcgaggt gatgcttctg   900
```

```
gagacatctc ggaggtacaa ccctgggagt gagagtatca ccttcctcaa ggatttcagt       960
tataaccggg aagactttgc caaagcaggg tctcgctctg tcgcccaggc tgaatgcagt      1020
ggtgtgatca atcatggctc aatgcagcct cgaccttctg ggctcaagtg atcctccttg      1080
agtagctggg actacagggc tgcaagtgga attcatcaac cccatcttcg agttctccag      1140
ggccatgaat gagctgcaac tcaatgatgc cgagtttgcc ttgctcattg ctatcagcat      1200
cttctctgca gaccggccca acgtgcagga ccagctccag gtggagaggc tgcagcacac      1260
atatgtggaa gccctgcatg cctacgtctc catccaccat ccccatgacc gactgatgtt      1320
cccacggatg ctaatgaaac tggtgagcct ccggaccctg agcagcgtcc actcagagca      1380
agtgtttgca ctgcgtctgc aggacaaaaa gctcccaccg ctgctctctg agatctggga      1440
tgtgcacgaa tga                                                        1453

<210> SEQ ID NO 5
<211> LENGTH: 192
<212> TYPE: DNA
<213> ORGANISM: Homo sapiens

<400> SEQUENCE: 5
gtggctggag aagggcaagg gatgaaggga gaagcagagt gggattatct gtgggagggg       60
cctccagaca tcgagctggg agagccaaat ctgctgggaa gcagggatga ggagaatcgg      120
cctccctgga agaggccatg ctccaagacc agccctccta gtccccgttt gaggtttgct      180
gcttgtgtgc ag                                                         192

<210> SEQ ID NO 6
<211> LENGTH: 109
<212> TYPE: DNA
<213> ORGANISM: Homo sapiens

<400> SEQUENCE: 6
ggtctcgctc tgtcgcccag gctgaatgca gtggtgtgat caatcatggc tcaatgcagc       60
ctcgaccttc tgggctcaag tgatcctcct tgagtagctg gactacag                  109

<210> SEQ ID NO 7
<211> LENGTH: 34
<212> TYPE: DNA
<213> ORGANISM: Artificial sequence
<220> FEATURE:
<223> OTHER INFORMATION: Designed oligonucleotide primer for PCR

<400> SEQUENCE: 7
cgaagcttgc caccatgtcc ttgtggctgg gggc                                   34

<210> SEQ ID NO 8
<211> LENGTH: 25
<212> TYPE: DNA
<213> ORGANISM: Artificial sequence
<220> FEATURE:
<223> OTHER INFORMATION: Designed oligonucleotide primer for PCR

<400> SEQUENCE: 8
cgggatcctt cgtgcacatc ccaga                                             25

<210> SEQ ID NO 9
<211> LENGTH: 24
<212> TYPE: DNA
<213> ORGANISM: Artificial sequence
<220> FEATURE:
<223> OTHER INFORMATION: Designed oligonucleotide primer for PCR
```

<400> SEQUENCE: 9
cagtgttgga ggctctgaca cacc						24

<210> SEQ ID NO 10
<211> LENGTH: 22
<212> TYPE: DNA
<213> ORGANISM: Artificial sequence
<220> FEATURE:
<223> OTHER INFORMATION: Designed oligonucleotide primer for PCR

<400> SEQUENCE: 10
ctgtgggttc tgaaggggc tc						22

<210> SEQ ID NO 11
<211> LENGTH: 23
<212> TYPE: DNA
<213> ORGANISM: Artificial sequence
<220> FEATURE:
<223> OTHER INFORMATION: Designed oligonucleotide primer for PCR

<400> SEQUENCE: 11
agagccaaat ctgctgggaa gcc						23

<210> SEQ ID NO 12
<211> LENGTH: 22
<212> TYPE: DNA
<213> ORGANISM: Artificial sequence
<220> FEATURE:
<223> OTHER INFORMATION: Designed oligonucleotide primer for PCR

<400> SEQUENCE: 12
ccgagatgtc tccagaagca tc						22

<210> SEQ ID NO 13
<211> LENGTH: 21
<212> TYPE: DNA
<213> ORGANISM: Artificial sequence
<220> FEATURE:
<223> OTHER INFORMATION: Designed oligonucleotide probe for TaqMan PCR

<400> SEQUENCE: 13
tcggcctccc tggaagaggc c						21

<210> SEQ ID NO 14
<211> LENGTH: 22
<212> TYPE: DNA
<213> ORGANISM: Artificial sequence
<220> FEATURE:
<223> OTHER INFORMATION: Designed oligonucleotide primer for PCR

<400> SEQUENCE: 14
ccctccaggg agatgctctg tg						22

<210> SEQ ID NO 15
<211> LENGTH: 21
<212> TYPE: DNA
<213> ORGANISM: Artificial sequence
<220> FEATURE:
<223> OTHER INFORMATION: Designed oligonucleotide primer for PCR

<400> SEQUENCE: 15
tgacccagac agcgctcttt g						21

<210> SEQ ID NO 16

-continued

```
<211> LENGTH: 24
<212> TYPE: DNA
<213> ORGANISM: Artificial sequence
<220> FEATURE:
<223> OTHER INFORMATION: Designed oligonucleotide probe for TaqMan PCR

<400> SEQUENCE: 16
tgtcatgaga cctccgggcc ttcc                                              24
```